(12) United States Patent
Lane et al.

(10) Patent No.: US 8,062,607 B2
(45) Date of Patent: Nov. 22, 2011

(54) LENS CARE METHODS AND KITS

(75) Inventors: Jennifer Dawn Lane, Stone Mountain, GA (US); Stephen Raymond Perreault, Norcross, GA (US); Elizabeth Hickson Beaullieu, Marietta, GA (US)

(73) Assignee: Novartis AG, Basel (CH)

( * ) Notice: Subject to any disclaimer, the term of this patent is extended or adjusted under 35 U.S.C. 154(b) by 383 days.

(21) Appl. No.: 12/309,347

(22) PCT Filed: Jul. 13, 2007

(86) PCT No.: PCT/US2007/016051
§ 371 (c)(1),
(2), (4) Date: Jan. 13, 2009

(87) PCT Pub. No.: WO2008/008525
PCT Pub. Date: Jan. 17, 2008

(65) Prior Publication Data
US 2009/0324466 A1  Dec. 31, 2009

Related U.S. Application Data

(60) Provisional application No. 60/830,739, filed on Jul. 13, 2006.

(51) Int. Cl.
| | |
|---|---|
| A61L 9/00 | (2006.01) |
| B01J 19/00 | (2006.01) |
| G01D 11/26 | (2006.01) |
| A45C 11/04 | (2006.01) |
| B65D 73/00 | (2006.01) |
| B65D 83/04 | (2006.01) |
| B65D 35/00 | (2006.01) |
| A61K 7/075 | (2006.01) |
| A61K 9/00 | (2006.01) |
| G01N 31/00 | (2006.01) |
| A01K 43/00 | (2006.01) |

(52) U.S. Cl. ............... 422/261; 422/1; 422/28; 422/30; 422/40; 422/559; 422/560; 422/119; 422/292; 422/300; 422/301; 424/70.24; 424/661; 424/840; 424/429; 252/95; 252/105; 252/408.1; 252/186.3; 510/112; 510/113; 206/5.1; 206/468; 206/532; 206/534.1; 206/538; 222/840; 222/839; 514/840; 514/839; 134/901

(58) Field of Classification Search ............... 422/1, 28, 422/30, 40, 554, 559, 560, 119, 261, 292, 422/300, 301; 424/70.24, 661, 840, 429; 252/95, 105, 408.1, 186.3; 510/112–113; 206/5.1, 468, 532, 534.1, 538; 222/92, 94; 514/840, 839; 134/901
See application file for complete search history.

(56) References Cited

U.S. PATENT DOCUMENTS 4,863,627 A    9/1989   Davies et al. ............... 252/95
(Continued)

FOREIGN PATENT DOCUMENTS
EP    1 645 296 A1    4/2006
(Continued)

OTHER PUBLICATIONS

PCT International Search Report.
(Continued)

*Primary Examiner* — Jill Warden
*Assistant Examiner* — Monzer Chorbaji
(74) *Attorney, Agent, or Firm* — Sheng-Hsin Hu; Jian Zhou

(57) ABSTRACT

The present invention provides a lens care kit for disinfecting and cleaning contact lenses. The lens care kit of the invention allows customers to visually identify when their lenses are disinfected, clean, and ready to wear. The invention is relied on color change to indicate the readiness of disinfection and cleaning of contact lenses.

16 Claims, 2 Drawing Sheets

U.S. PATENT DOCUMENTS

| | | | | |
|---|---|---|---|---|
| 5,362,444 | A | 11/1994 | Amtower | 422/30 |
| 5,395,621 | A | 3/1995 | Amtower | 424/613 |
| 5,531,963 | A * | 7/1996 | Powell, Jr. | 422/30 |
| 5,630,884 | A | 5/1997 | Huth | 134/27 |
| 5,681,591 | A | 10/1997 | Park et al. | 424/616 |
| 6,099,800 | A | 8/2000 | Cheng | 422/30 |
| 6,440,411 | B2 | 8/2002 | Scherer et al. | 424/94.4 |
| 2004/0241206 | A1 * | 12/2004 | Ketelson et al. | 424/429 |
| 2005/0054546 | A1 | 3/2005 | Glick et al. | 510/112 |

FOREIGN PATENT DOCUMENTS

NL      C 1023255      10/2004

OTHER PUBLICATIONS

PCT Written Opinion of the International Searching Authority.

* cited by examiner

LENS CARE METHODS AND KITS

This application is a national stage filing under 35 U.S.C. 371 of International Application No. PCT/US2007/016051 filed Jul. 13, 2007, which claims benefits of U.S. Provisional Application No. 60/830739 Jul. 13, 2006.

This invention relates generally to a system, methods, and kits useful for cleaning and disinfecting a contact lens.

BACKGROUND OF THE INVENTION

Contact lenses provide a means for vision correction for a wide range of consumers. The advantages of contact lens wear are numerous. Improved convenience and improved appearance in comparison to spectacle glasses are probably the two most important advantages to most consumers. However, contact lenses require stringent care regimes in order to ensure comfort and avoid ocular infections. Proper care of contact lenses typically requires the consumer to periodically clean and disinfect the lenses, to prevent infection or other deleterious effects on ocular health which may be associated with contact lens wear.

In recent years, multiple-purpose solutions, which clean, disinfect, and rinse contact lenses all without mechanically rubbing lenses, have been developed as a new type of lens care systems. These new systems start dominating the most of the lens care market. Such popularity is most likely derived from the easiness and convenience provided by these new systems to consumers. In order to achieve a satisfactorily disinfecting result, a contact lens has to be in a MPS solution for a sufficient time period. However, consumers do not have a direct way to determine if their lenses have been in the lens care solution long enough to disinfect the lenses. It would be desirable to provide customers means by which they could visually identify when their lenses are clean and ready to wear.

Therefore, there exists a need for a lens care kit capable of discoloring or changing color over the time period required for disinfection of contact lenses.

SUMMARY OF THE INVENTION

Generally described, the present invention provides a lens care kit for cleaning and disinfecting contact lenses, comprising a colored lens care solution including a water-soluble colorant and a solid absorbing agent, wherein, when in contact with the colored lens care solution, the solid absorbing agent adsorbs the colorant over a time period sufficient to substantially discolor the colored lens care solution, thereby indicating that lenses under disinfecting and cleaning by the colored lens care solution are ready for use. The lens care kit of the invention allows customers to visually identify when their lenses are disinfected, clean, and ready to wear.

DETAILED DESCRIPTION OF PREFERRED EMBODIMENTS

Figure 1:
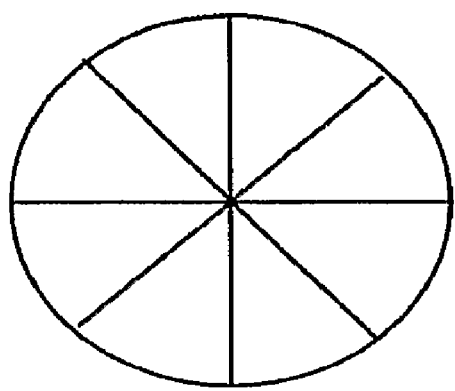
FIG. 1 illustrates a pinwheel which contains solid absorbing agent thereon and can be fitted in the bottom of a lens case for treating a contact lens according to a preferred embodiment of the invention.

The present invention may be understood more readily by reference to the following detailed description of the invention taken in connection with the accompanying drawing figures, which form a part of this disclosure. Unless defined otherwise, all technical and scientific terms used herein have the same meaning as commonly understood by one of ordinary skill in the art to which this invention belongs. Generally, the nomenclature used herein is well known and commonly employed in the art. Conventional methods are used for carrying out the disclosed procedures, such as those provided in the art and various general references. It is to be understood that this invention is not limited to the specific devices; methods, conditions or parameters described and/or shown herein, and that the terminology used herein is for the purpose of describing particular embodiments by way of example only and is not intended to be limiting of the claimed invention. Also, as used in the specification including the appended claims, reference to singular forms such as "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The invention, in one aspect, provides a lens care kit for cleaning and disinfecting contact lenses, comprising a colored lens care solution including a water-soluble colorant and a solid absorbing agent, wherein, when in contact with the colored lens care solution, the solid absorbing agent adsorbs the colorant over a time period sufficient to substantially discolor the colored lens care solution, thereby indicating that lenses under disinfecting and cleaning by the colored lens care solution are ready for use.

A lens care kit of the invention can be used to disinfect and clean contact lenses including hard (PMMA) contact lenses, soft (hydrophilic) contact lenses, and rigid gas permeable (RGP) contact lenses. The soft contact lenses are hydrogel contact lens or silicone hydrogel contact lenses.

A "hydrogel" refers to a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers.

A "silicone hydrogel" refers to a hydrogel obtained by copolymerization of a polymerizable composition comprising at least one silicone-containing vinylic monomer or at least one silicone-containing macromer.

"Hydrophilic," as used herein, describes a material or portion thereof that will more readily associate with water than with lipids.

The lens care kit of the invention allows customers to visually identify when their lenses are disinfected, clean, and ready to wear. The invention is relied on color change to indicate the readiness of disinfection and cleaning of contact lenses. Preferably, the initial color is blue or green or purple. It is understood that any other color can be used.

In accordance with the invention, the lens care solution has a color that is gradually faded over a controlled time period. Preferably, at the end of the controlled time period, the color of the lens care solution is substantially disappeared and becomes substantially clear (substantially colorless but transparent). The controlled time period is sufficient long for disinfecting contact lenses and is preferably at least about 2 hour, more preferably about 4 hours, even more preferably about 6 hours.

A colored lens care solution of the invention comprises a water-soluble colorant. In accordance with the invention, the colorant should be a non-toxic dye and does not foul or stain contact lenses and lens cases. Examples of dyes include, without limitation, coomassie blue, EvoBlue30, malachite green, Victoria blue, remazol brilliant blue, acid blue 62, sanoline green, LinaBlue AE, luminal, lumigen, bromophenol blue, methylene blue, bromocresol blue, thymol blue, methyl crystal purple, tetraphenolporphyrin, triphenylamine dyes—brilliant green, triphenylamine dyes—crystal violet, benzoyl anthraquinone, dibezanthron dye (celadon jade green), indanthrene blue, brilliant cresyl blue, 2,6 dichlorophenolindophenol Na Salt, N,N dimethyl-1,4-phenylene diammonium dichloride, diphenylamine, toluidine blue, diphenyl benzidine, safranin, thionine, variamine blue salt B, alizarin, isatin, kermesic acid, FD&C Blue #1, FD&C Blue #2, FD&C green #3, D&C Blue #4, D&C green #5, Ex D&C violet #2, D&C green #8, D&C violet #2, Sandolan blue E HRC, Handolan Milling blue NVC, Dimarine blue K35L, dimarine brilliant blue K-BL, cartasol blue GDF, Cartasol brilliant violent SBF, diphenylamine, diphenylbenzidine, and sprillium blue. Preferred dyes are FD&C Blue No 1, Sanoline Blue, and Remazol Blue. Most preferred dye is FD&C Blue No 1.

Dyes can be modified by attaching a polymeric tail to them in order to prevent the dyes from being absorbed by lens material based on size alone. For example, a polyethylene glycol urea (PEG-urea, ~3000 m.w.) or an amino-dextran (500,000 m.w.) can be covalently attached to a dye through the succinimdyl ester functional group or other functional groups. A person skilled in the art will know how to covalently attach a polymer onto a dye.

In accordance with the invention, one or more colorants can be used together in the colored lens care solution to create desired color. A person skilled in the art will knows well how to select types of colorants and amounts thereof to achieve a desired color.

In accordance with the invention, a colored lens care solution is ophthalmic safe. The term "ophthalmically safe" with respect to a lens care solution is meant that a contact lens treated with the solution is safe for direct placement on the eye without rinsing, that is, the solution is safe and sufficiently comfortable for daily contact with the eye via a contact lens. An ophthalmically safe solution has a tonicity and pH that is compatible with the eye and comprises materials, and amounts thereof, that are non-cytotoxic according to international, ISO standards and U.S. FDA regulations.

The term "compatible with the eye" means a solution that may be in intimate contact with the eye for an extended period of time without significantly damaging the eye and without significant user discomfort.

A colored lens care solution can be a prepared from any lens care solutions including commercially available lens care solutions by adding one or more colorants therein. A lens care solution can be a multiple purpose solution (free of hydrogen peroxide) or a hydrogen peroxide containing solution.

Where a lens care solution is a hydrogen peroxide containing solution, the colored lens care solution is preferably prepared immediately prior to lens disinfection in a lens case by mixing two solutions, one hydrogen peroxide containing solution free of colorant and the other solution containing colorant and free of hydrogen peroxide. Such mixing can be achieved used a container having two separate compartments, one for hydrogen peroxide containing solution and the other for the colorant containing solution free of hydrogen peroxide. The container can further comprises a mixing mechanism known to a person skilled in the art to mix the two solutions when pouring out the two solutions from the container. By separately storing a hydrogen peroxide containing solution and a colorant containing solution and mixing them on-demand to form a colored lens care (disinfecting) solution, one may minimize or eliminate the possibility of the colorant being oxidize slowly by hydrogen peroxide and thereby greatly increases the shelf lifetimes of the solutions.

In accordance with the invention, a hydrogen-peroxide containing solution can further comprises other components known to a person skilled in the art, for example, tonicity agent (e.g., sodium chloride, potassium chloride, mannitol, xylitol, dexpenthanol, dextrose, glycerin, propylene glycol, and mixture thereof), conditioning/wetting agents (polyvinyl alcohol, polyoxamers, polyvinyl pyrrolidone, hydroxypropyl cellulose, and mixture thereof), buffering agents, surfactants, and the like.

Where a lens care solution is a hydrogen-peroxide-free disinfecting solution, such as, for example, a multiple purpose solution, a colorant can be directly added into it to prepare a colored lens care solution of the invention, because of the absence of hydrogen peroxide.

In a preferred embodiment, the lens care solution of the invention is a multipurpose solution capable of disinfecting, cleaning, and rinsing a contact lens.

The term "disinfecting solution" means a solution containing one or more microbiocidal compounds, that is effective for reducing or substantially eliminating the presence of an array of microorganisms present on a contact lens, which can be tested by challenging a solution or a contact lens after immersion in the solution with specified inoculums of such microorganisms.

A solution that is useful for cleaning, chemical disinfection, storing, and rinsing an article, such as a contact lens, is referred to herein as a "multi-purpose solution." Such solutions may be part of a "multi-purpose solution system" or "multi-purpose solution package." The procedure for using a multi-purpose solution, system or package is referred to as a "multi-functional disinfection regimen." Multi-purpose solutions do not exclude the possibility that some wearers, for example, wearers particularly sensitive to chemical disinfectants or other chemical agents, may prefer to rinse or wet a contact lens with a another solution, for example, a sterile saline solution prior to insertion of the lens. The term "multi-purpose solution" also does not exclude the possibility of periodic cleaners not used on a daily basis or supplemental cleaners for removing proteins, for example enzyme cleaners, which are typically used on a weekly basis.

A colored hydrogen-peroxide-free disinfecting solution of the invention can be used to disinfect contact lenses against a wide range of microorganisms including but not limited to

*Fusarium solani, Staphylococcus aureus, Pseudomonas aeruginosa, Serratia marcescens* and *Candida albicans*. For the purposes of the present invention the term "disinfect" means the rendering non-viable of substantially all pathogenic microbes that are in the vegetative state, including gram negative and gram positive bacteria, as well as fungi. The chemical compounds and compositions that render such pathogenic microbes inactive are known as microbicides.

A colored disinfecting or MPS solution of the invention must contain a microbicide in a concentration sufficient to effect the desired disinfection of a contact lens. The specific concentrations required for the microbicides useful in this invention must be determined empirically for each microbicide. Some of the factors affecting the effective concentration are specific activity of the microbicide against the specified pathogens, the molecular weight of the microbicide, and the solubility of the microbicide. It is also important that the chosen microbicides be employed in a physiologically tolerable concentration. The list of microbicides which may be employed in the present invention include, but is not limited to biguanides, biguanide polymers, salts thereof, N-alkyl-2-pyrrolidone, polyquarternium-1, bronopol, benzalkonium chloride, and hydrogen peroxide. The presently useful antimicrobial biguanides include biguanides, biguanide polymers, salts thereof, and mixtures thereof. Preferably, the biguanide is selected from alexidine free-base, salts of alexidine, chlorhexidine free-base, salts of chlorhexidine, hexetidine, hexamethylene biguanides, and their polymers, and salts thereof. Most preferably, the biguanide is a hexamethylene biguanide polymer (PHMB), also referred to as polyaminopropyl biguanide (PAPB).

Typical solutions of this invention contain the microbicides PHMB in an amount of from about 0.01 to about 10 ppm, preferably from about 0.05 to about 5 ppm, more preferably from about 0.1 to about 2 ppm, even more preferably from about 0.2 to about 1.5 pp.

Although PHMB has a broad spectrum of activity and non-specific mode of action against bacteria, PHMB might be able to cause some level of corneal staining (Lyndon Jones, et. al. "Asymptomatic corneal staining associated with the use of balafilcon silicon-hydrogel contact lenses disinfected with a polyaminopropyl biguanide—preserved care regimen", Optometry and Vision Science 79: 753-61 (2002)). Therefore, it would be desirable to lower the amount of PHMB in a lens care solution while maintaining the antimicrobial efficacy of the lens care solution.

The present solutions preferably include an effective amount of a chelating component. Any suitable, preferably ophthalmically acceptable, chelating component may be included in the present compositions, although ethylenediaminetetraacetic acid (EDTA), salts thereof and mixtures thereof are particularly effective. EDTA is low level non-irritating chelating agent and can be synergistic with PHMB to increase antimicrobial efficacy. Typical amount of EDTA is from about 0.001% to about 1% by weight, preferably from about 0.002% to about 0.5% by weight, more preferably from about 0.004% to about 0.1, even more preferably from about 0.005 to about 0.05, based on the total amount of contact lens care composition.

The solution of the present invention preferably contains a buffering agent. The buffering agents maintain the pH preferably in the desired range, for example, in a physiologically acceptable range of about 6.0 to about 8.0. Any known, physiologically compatible buffering agents can be used. Suitable buffering agents as a constituent of the contact lens care composition according to the invention are known to the person skilled in the art. Examples are boric acid, borates; e.g. sodium borate, citric acid, citrates, e.g. potassium citrate, bicarbonates, e.g. sodium bicarbonate, TRIS (trometamol, 2-amino-2-hydroxymethyl-1,3-propanediol), bis-aminopolyols, phosphate buffers, e.g. $Na_2HPO_4$, $NaH_2PO_4$, and $KH_2PO_4$ or mixtures thereof. The amount of each buffer agent is that amount necessary to be effective in achieving a pH of the composition of from about 6.5 to about 7.5. Typically, it is present in an amount of from 0.001% to 2%, preferably from 0.01% to 1%; most preferably from about 0.05% to about 0.30% by weight.

The preferred buffering agents are bis-aminopolyols of formula (I)

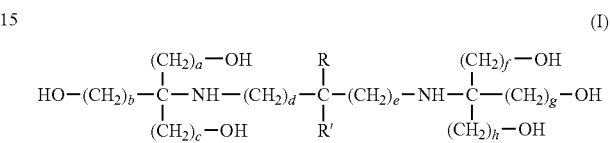

(I)

wherein a, b, c, d, e, f, 9, and h are independently an integer from 1 to 6; and R and R' are independently selected from the group consisting of —H, —$CH_3$, —$(CH_2)_{2-6}$—H, and —$(CH_2)_{1-6}$—OH. In the present invention, the buffering agents described by formula (I) may be provided in the form of various water-soluble salts. A most preferred bis-aminopolyol is 1,3-bis(tris[hydroxymethyl]methylamino)propane (bis-TRIS-propane).

It has been found that bis-TRIS-propane can exhibit a synergy with certain microbicides (e.g., PHMB) and fungicides, resulting in a microcidal activity significantly higher than the activity of these same active ingredients used in conjunction with other buffers. BIS-TRIS propane is described under biological buffers in Biochemicals and Reagents, Sigma-Aldrich Co., 2000-2001: edition. The specific structure of bis-TRIS-propane is shown in formula II.

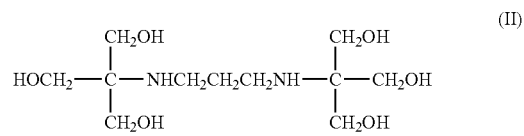

(II)

The dissociation constants for this dibasic compound are $pKa_1=6.8$ and $pKa_2=9.5$ which renders aqueous solutions of this compound useful as a buffering agent in a broad pH range from about 6.3 to 9.3. bis-TRIS-propane at a concentrations used in this invention is harmless to the eye and to known contact lens materials and is, therefore, ophthalmically compatible.

A colored lens care solution of the invention preferably comprises a lubricant. "Lubricants" as used herein refer to any compounds or materials which can enhance surface wettability of a contact lens and/or the eye or reduce the frictional character of the contact lens surface. Examples of lubricants include without limitation mucin-like materials and hydrophilic polymers.

Exemplary mucin-like materials include without limitation polyglycolic acid, polylactides, collagen, and gelatin. A mucin-like material may be used to alleviate dry eye syndrome. The mucin-like material preferably is present in effective amounts.

Exemplary hydrophilic polymers include, but are not limited to, polyvinylalcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methaacrylamide, a copolymer of acrylamide or methacrylamide with one or more hydrophilic vinylic monomers, mixtures thereof.

The solution may also contain one or more viscosity-enhancing agents. Suitable viscosity-enhancing components include, but are not limited to, polyvinylpyrrolidone, water soluble natural gums, cellulose-derived polymers; and the like. Useful natural gums include guar gum, gum tragacanth and the like. Examples of useful cellulose-derived polymers as viscosity-enhancing agents include without limitation cellulose ethers.

Exemplary preferred cellulose ethers are methyl cellulose (MC), ethyl cellulose, hydroxymethylcellulose, hydroxyethyl cellulose (HEC), hydroxypropylcellulose, hydroxypropylmethyl cellulose (HPMC), or a mixture thereof. More preferably, a cellulose ether is hydroxyethyl cellulose (HEC), hydroxypropylmethyl cellulose (HPMC), and mixtures thereof. The cellulose ether is present in the composition in an amount of from about 0.01% to about 5% by weight, preferably from about 0.05% to about 3% by weight, even more preferably from about 0.1% to about 1% by weight, based on the total amount of contact lens care composition. It is believed that a cellulose ether can be used to increase the viscosity of a lens care and also can serve as a lubricant in the lens care composition.

A very useful viscosity-enhancing component is polyvinylpyrrolidone (PVP). The polyvinylpyrrolidone (PVP) used in the compositions of the invention is a linear homopolymer or essentially a linear homopolymer comprising at least 90% repeat units derived from 1-vinyl-2-pyrrolidone monomers, the polymer more preferably comprising at least about 95% or essentially all of such repeat units, the remainder selected from polymerization-compatible monomers, preferably neutral monomers, such as alkenes or acrylates. Other synonyms for PVP include povidone, polyvidone, 1-vinyl-2-pyrrolidinone, and 1-ethenyl-2-pyrolionone (CAS registry number 9003-39-8). The PVP used in the present invention suitably has a weight average molecular weight of about 10,000 to 250,000, preferably 30,000 to 100,000. Such materials are sold by various companies, including ISP Technologies, Inc. under the trademark PLASDONE™ K-29/32, from BASF under the trademark KOLLIDON™ for USP grade PVP, for example KOLLIDON™ K-30 or K-90. While the invention is not limited to any specific PVP, K-90 PVP is preferred, more preferably pharmaceutical grade.

The colored lens care solutions according to the invention are preferably formulated in such a way that they are isotonic with the lachrymal fluid. A solution which is isotonic with the lachrymal fluid is generally understood to be a solution whose concentration corresponds to the concentration of a 0.9% sodium chloride solution (308 mOsm/kg). Deviations from this concentration are possible throughout, provided that the contact lenses to be treated are not damaged.

The isotonicity with the lachrymal fluid, or even another desired tonicity, may be adjusted by adding organic or inorganic substances which affect the tonicity. Suitable occularly acceptable tonicity agents include, but are not limited to sodium chloride, potassium chloride, glycerol; propylene glycol, polyols, dexpanthenol, mannitols, xylitol, sorbitol, and mixtures thereof. Preferably, the majority of the tonicity of the solution is provided by one or more compounds selected from the group consisting of non-halide containing electrolytes (e.g., sodium bicarbonate) and non-electrolytic compounds. The tonicity of the solution is typically adjusted to be in the range from about 200 to about 450 milliosmol (mOsm), preferably from about 250 to 350 mOsm.

In accordance with the invention the colored lens care solution can further comprise a surfactant for cleaning the contact lens. Any suitable known surfactants can be used in the invention. Examples of suitable surfactants include, but are not limited to poloxamers under the tradename Pluronic from BASF Corp. (Pluronic™ and Pluronic-R™) which are nonionic surfactants consisting of block copolymers of propylene oxide and ethylene oxide; poloxamine which is a block copolymer derivative of ethylene oxide and propylene oxide combined with ethylene diamine; tyloxapol, which is 4-(1,1,3,3-tetramethylbutyl)phenol polymer with formaldehyde and oxirane; ethoxylated alkyl phenols, such as various surface active agents available under the tradenames TRITON (Union Carbide, Tarrytown, N.Y., USA) and IGEPAL (Rhone-Poulenc, Cranbury, N.J., USA); polysorbates such as polysorbate 20, including the polysorbate surface active agents available, under the tradename TWEEN (ICI Americas, Inc., Wilmington, Del., USA.); alkyl glucosides and polyglucosides such as products available under the tradename PLANTAREN (Henkel Corp., Hoboken, N.J., USA); and polyethoxylated castor oils commercially available from BASF under the trademark CREMAPHOR.

Preferred surfactants include homopolymers of polyethylene glycol or polyethyleneoxide, and certain poloxamers such as materials commercially available from BASF under the tradenames PLURONIC® 17R4, PLURONIC® F-68NF, PLURONIC® F68LF, and PLURONIC® F127, with PLURONIC® F-68NF (National Formulary grade) being the most preferred. More preferably, a combination of PLURONIC® 17R4 and PLURONIC® F127 is used. When present, poloxamers may be employed at from about 0.001%"to about 5%" by weight, preferably from about 0.005% to about 1% by weight, more preferably from about 0.05% to about 0.6% by weight.

The colored lens care solutions according to the invention are produced in known manner, in particular by means of conventional mixing of the constituents with water or dissolving the constituents in water.

In accordance with the invention, any solid absorbing agents can be used in the invention. Preferably, the solid absorbing agent is activated charcoals, zeolites, silicates, or combination thereof.

Activated carbon is more preferably used in this invention. Activated carbon can be prepared from various of wood, coconut and other shells, and various grade of coal. Activated carbon can be in various forms: such as for example, ultra-fine mesh powders, granular, particulate. Activated carbon can be also in solid form, such as a honeycomb or disc which can be easily fit into the well of a lens case. Density and porosity are varied that can influence activated carbon's adsorptive properties. In accordance with the invention, activated carbon used in the invention is preferably free of fine carbon particulate dust. The release of fine particles of activated carbon into a lens care solution would be undesirable.

In accordance with the invention, activated carbon can be added into a lens case where a contact lens will be disinfected with a colored lens care solution of the invention. The activated carbon can be added in the lens case prior to or posterior to filling of the lens case with the colored lens care solution. The order is not important.

A lens case typically comprises a main body portion which includes a pair of separate and discrete wells (cavities or reservoirs) each adapted to receive one contact lens and an amount of a lens care solution. Each well has an open end having a substantially circular, oval or rain-drop shape periphery defining an opening. The lens case further comprises one or two caps adapted to be affixed to the wells at their open ends so as to provide a substantially liquid-impermeable seal. The caps each further include a sealing rim or surface adapted to mate with peripheries surrounding wells. The lens case may be constructed of a material which is sturdy and impervious to chemicals contained in a lens solution. For example, polystyrene, high-density polyethylene, or polypropylene can be the construction material of choice, although others may be used.

Preferably, activated carbon can be placed in a lens case's compartment in fluid communication with the well of a lens case for holding a contact lens and a given amount of a lens care solution. In a preferred embodiment, there is a semi-permeable membrane between the well and the activated carbon-holding compartment. Preferably, the membrane can function as a size exclusion filter, which allows the water soluble dye in the colored lens care solution and other substances with small molecular weight to pass therethrough to get in contact with the activated car bon, whereas hinders surfactants and microbicides with larger molecular weight (e.g., large molecular weight PHMB) from passing through the membrane and getting in contact with the activated carbon. With semi-permeable membrane, one can minimize the adsorption of microbicides and surfactants by the activated carbon and thereby retain the antimicrobial and cleaning efficacy of the lens care solution.

Alternatively, activated carbon can be encapsulated with a layer of a polymer so as to differentially decrease the rate of absorption of microbicides and surfactants by activated carbon.

Figure 2:
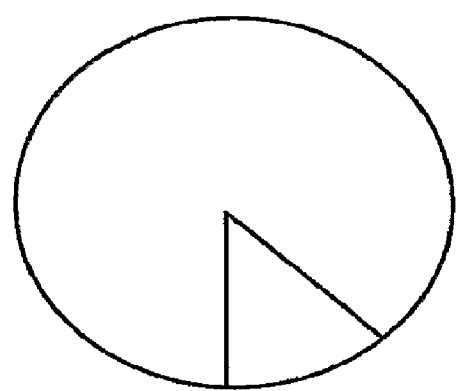
FIG. 2 illustrates the top view of the pinwheel shown in FIG. 1.
Figure 3:
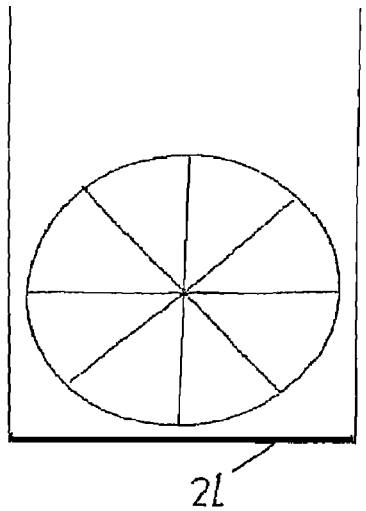
FIG. 3 illustrates the pinwheel shown in FIG. 1 within the confines of the lens case 21.
Figure 4:
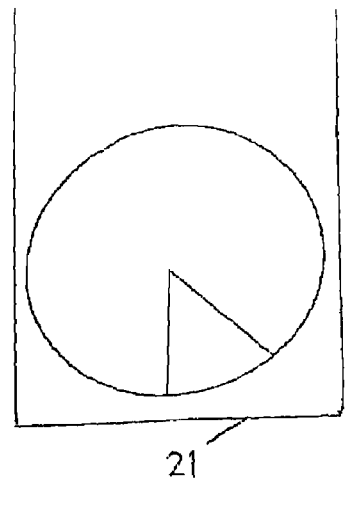
FIG. 4 illustrates the pinwheel shown in FIG. 2 within the confines of the lens case 21.
Figure 6:
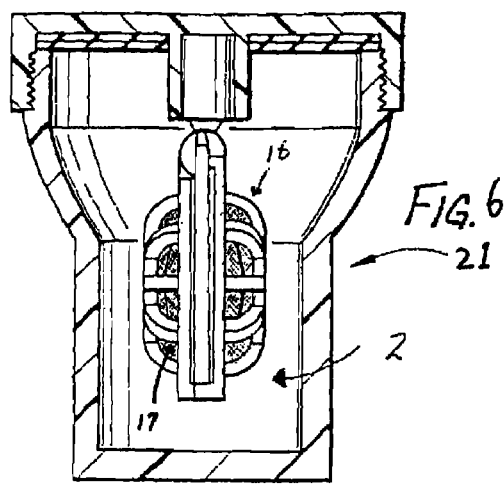
FIG. 6 illustrates a lens case (21) having a well (2) and a compartment (16) with a semi-permeable membrane (17) which is located between the well (2) and the compartment (16).
Figure 5:
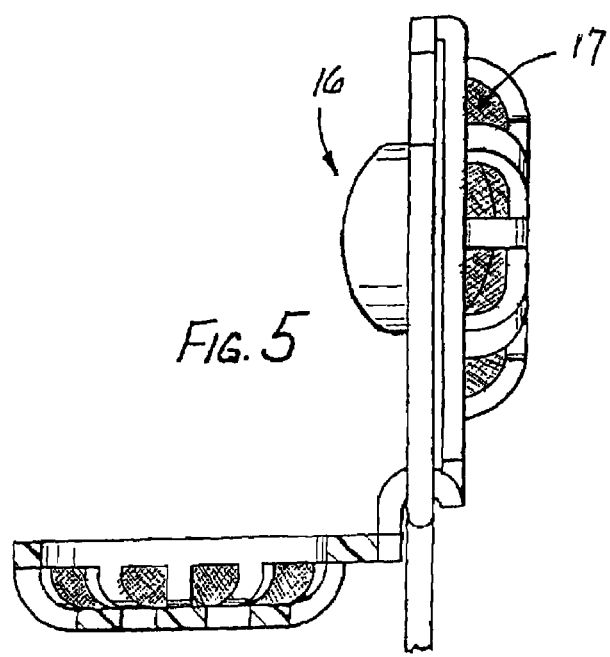
FIG. 5 illustrates a compartment (16) with a semi-permeable membrane (17).

In a preferred embodiment, an absorbing agent is placed into a pinwheel configuration (FIG. 1) within the confines of a lens case. This pinwheel configuration is covered with a top that allows only a small piece of the pinwheel to be exposed to the lens care solution (FIG. 2). After a number of uses (i.e., disinfection of a contact lens), the top of the pinwheel is rotated to allow a fresh amount of absorbing agent to be exposed to the lens care solution and as such, the colorant can be absorbed onto the fresh absorbing agent. FIGS. 1 and 2 show a preferred embodiment of the invention. It is understood that other configurations can also be used. The pinwheel can be divided into any number of sectors, e.g., from 2 to 15.

The kit can optionally include instructions for how to use the lens care solution to clean and lubricate contact lenses directly in eyes.

The contact lens can be contacted with the solution by immersing the lens in a colored lens care solution of the invention in a lens case. Although not necessary, the solution containing the contact lens can be agitated, for example, by shaking the lens case containing the solution and contact lens, to at least facilitate removal of deposit material from the lens.

In another aspect, the invention provides a method for cleaning and/or disinfecting a contact lens. The method comprises the steps of: bringing one or more contact lenses into contact with a colored lens care solution in a lens case containing a solid absorbing agent; and observing change in the color of the colored lens care solution, substantially discoloring of the colored lens care solution indicating that the lenses under disinfecting and cleaning by the colored lens care solution are ready for use.

The above described various embodiments can be used in this aspect of the invention.

The solutions and methods of the present invention may be used in conjunction with enzymes to remove debris or deposit material from the contact lens as the solutions of the present invention have no negative effect on the proteolytic activity of enzymes, such as UNIZYME®. After such contacting step, the contact lens optionally may be manually rubbed with saline, or even rinsed without rubbing, to remove further deposit material from the lens. The cleaning method can also include rinsing the lens substantially free of the liquid aqueous medium prior to returning the lens to a wearer's eye.

The previous disclosure will enable one having ordinary skill in the art to practice the invention. In order to better enable the reader to understand specific embodiments and the advantages thereof, reference to the following examples is suggested.

EXAMPLE 1

Various dyes are tested to determine if they can stain contact lenses (Focus® Night and Day™ (FND), Focus® Monthly, Focus® Dailies®, and Cibasoft® lenses, all from CIBA Vision) by soaking them in a dye solutions made in Aquify® MPS (CIBA Vision) or phosphate buffered saline (PBS). It has found that Coomassie Blue stains Focus® Night and Day™, Focus® Monthly, and Focus® Dailies®, but does not stain Cibasoft® lenses; Methylene Blue stains Focus® Monthly, Focus® Dailies® and Cibasoft® lenses, but does not stain Focus® Night and Day™; EvoBlue30 and Acid Blue 62 each stain all tested lenses; Malachite Green, FD&C Blue No 1, Victoria Blue, Remazol Brilliant Blue, Sanolin Green, and LinaBlue AE do not stain any tested lenses.

A dye which is absorbed onto the above described lenses are dropped as potential candidates.

FD&C Blue No 1, Sanolin Blue, and Remazol Blue dissolved in Aquify® MPS (CIBA Vision) are submitted for micro testing as a stand alone solution. FD&C Blue No 1 passes all micro testing.

Lens soaking studies have been started with FD&C Blue No 1, Vitosyn Blue, and LinaBlueAE in Aquify® MPS. No color uptake has been observed with FD&C Blue No 1 for lenses soaked for 94 days. No uptake has been observed with VitosynBlue for lenses soaked for 52 days. No uptake has been observed with LinaBlueAE for 21 days.

Lenses soiled with artificial tear fluid for 24 hours are also exposed to FD&C Blue No 1 in Aquify® MPS to determine if presence of protein on the lenses would absorb FD&C Blue No 1. After a soak of 1 day in FD&C Blue No 1 in Aquify® MPS, no visible color uptake is observed.

EXAMPLE 2

Dye Modification

Experiments are carried out to modify dyes by attaching a polymeric tail in order to prevent the dyes from being absorbed by lens material based on size alone. A polyethylene glycol urea (PEG-urea, ~3000 m.w.) or an amino-dextran (500,000 m.w.) are covalently attached to EVOBlue30 (EB30) and Malachite Green through the succinimdyl ester functional group of these two dyes. After purification, each polymeric dye is exposed to contact lenses. With a polymeric tail, the modified EB30 is not absorbed by lenses, but the modified malachite green is still absorbed by lenses. The polymeric tail does decrease the amount of malachite green absorbed by lenses, compared to the dye without the presence of the tail.

EXAMPLE 3

Cytotoxicity of a colored lens care solution is evaluated by using the Standard USP Elution Test ("Biological Reactivity Tests, in vitro: Elution Test", USP). A colored lens care solution is diluted with serum-supplemented cell culture medium at 25% test solution concentration. Each culture is examined microscopically after 48 hours using trypan blue for the presence of morphological changes, reduction in cell density or cell lysis induced by the test solution. Solutions 10-12 prepared in Example 1 all pass the USP elution tests.

Colored lens care solutions are prepared by adding into Aquify® MPS one of the following dyes: FD&C Blue No 1, Remazol Blue, Sanolin Blue, LinaBlue AE, Acid Blue 62, Sanolin Green, Vitosyn Blue and Victoria Blue.

All tested dyes are considered non-cytotoxic with the exception of Victoria Blue which is very cytotoxic.

EXAMPLE 4

Color Selection and Intensity

It is determined that the most visually appealing product can be made by adding FD&C Blue No 1 in a lens care solution in an amount sufficient to provide an absorbance value of ~0.05 AU in the wavelength range of 620-640 nm. This intensity gives a slightly visible color to the solution in the lens case which is not overwhelming.

Color Stability

The colorant stability has also been tested for FD&C Blue No 1 in Aquify® MPS stored at 25° and 45° C. for 94 days. The visible spectrum measured spectrophotometrically has not changed significantly from the time 0. This gives us a shelf-life estimation based on colorant stability alone of approximately a year for FD&C Blue No 1 in Aquify® MPS.

The colorant stability has also been tested for Vitosyn Blue in a lens care solution described above stored at 25° and 45° C. for 52 days. The visible spectrum measured spectrophotometrically has not changed from time 0. This gives a shelf life estimation based on colorant stability alone for approximately 7 months for Vitosyn Blue in the lens care solution.

EXAMPLE 5

Decolorization Kinetics of AC 15 samples of activated carbon from various sources are evaluated for their decolorization kinetics, using a colored lens care solution containing FD&C Blue No 1. The amount of activated charcoal is about 0.06 g/mL lens care solution. All kinetic experiments are carried out in 50 mL volumes using charcoal contained in a teabag. Each teabag is rinsed with de-ionized water prior to decolorization in an attempt to reduce the charcoal dust which is inherently present on the charcoal. Results are reported in Table 1.

Activated carbon with various forms are also tested. The results are shown in Table 2.

TABLE 1

| Activated Carbon | Decoloring Rate | Decoloring Time | Fines deposited in solution |
|---|---|---|---|
| BX-7540 (Westvaco) | ++ | 6 hr | No |
| WV-B 1500 20 × 50 (Westvaco) | +++ | 5-6 hrs | Yes |
| Aquaguard 40 (Westvaco) | +++ | 5-6 hrs | Yes |
| Nuchar WV-B 14 × 35 (Westvaco) | ++ | Greater than 6 hrs | Yes |
| BX-7530 (Westvaco) | ++ | Greater than 6 hrs | Yes |
| Nuchar RGC 20 × 50 (Westvaco) | ++++ | 4-5 hrs | Yes |
| Aquaguard 20 × 50 (Westvaco) | ++ | Greater than 6 hrs | Yes |
| Nuchar RGC 12 × 40 (Westvaco) | +++ | 5-6 hrs | Yes |
| CAL 12 × 40 (Calgon Carbon Co.) | +++ | 5-6 hrs | Yes |
| CPG LF 12 × 40 (Calgon Carbon Co.) | + | Greater than 6 hrs | Yes |
| SGL 8 × 30 (Calgon Carbon Co.) | ++ | 6 hrs | Yes |
| Norit GAC 1240+ (Norit Americas Inc.) | +++ | 5-6 hrs | Yes |
| Darco 12 × 20 LI (Norit Americas Inc.) | + | Greater than 6 hrs | Yes |
| Norit RO × 0.8 (Norit Americas Inc.) | ++++ | 5-6 hrs | Yes, Heavy |
| Acticarbon BX no 217 (Atofina Chemicals Inc.) | ++++ | 5 hrs | Yes |
| Plekx 1 (KX Industries) | ++ | Slightly greater than 6 hrs | Minimal |
| Plekx 10 (KX Industries) | ++ | Slightly greater than 6 hrs | Minimal |
| P & G White | + | Greater than 6 hrs | Heavy |
| P & G Blue | + | Greater than 6 hrs | Heavy |

++++: Extremely fast; +++: fast; ++: Moderate; +: Slow

TABLE 2

| Activated carbon | Form | Time to Complete Decolorization | Comments |
|---|---|---|---|
| BX-7540 (Westvaco) | Granular | 6 hr | No fines deposited in solution |
| Nuchar RGC 20 × 50 (Westvaco) | Granular | 4-5 hrs | Fines deposited in solution |
| Acticarbon BX no 217 (Atofina Chemicals Inc.) | Granular | 5 hrs | Fines deposited in solution |
| Zorflex FM1 4 cm × 4 cm cloth (Calgon) | Cloth | 6+ hours | No fines deposited in solution |
| Zorflex FM1 Silver 4 cm × 4 cm cloth (Calgon) | Cloth | 6+ hours | No fines deposited in solution |
| Zorflex FM7 4 cm × 4 cm cloth (Calgon) | Cloth | 6+ hours | No fines deposited in solution |
| Zorflex FM7 Silver 4 cm × 4 cm cloth (Calgon) | Cloth | 6+ hours | No fines deposited in solution |
| TAC 600 | Granular | 4-6 hours | |
| WVB 20 × 50 (Mead Westvaco) | Granular | 4-6 hours | |
| Aquabond (Omnipure) | Granular | 4-6 hours | |
| RGC Carbon Disks (80% wt carbon) (Mead Westvaco) | Disc/Tablet | 4-6 hours | |
| RGC Carbon Honeycombs (30% wt carbon) (Mead Westvaco) | Honeycomb Tablet | 4-6 hours | |

Several colored lens care solutions containing FD&C Blue No 1 are prepared, shown in Table 3. Those solutions have been studied for decolorization kinetics and the appropriate decolorization kinetics are achieved with those solutions. It is found that Pluronic F127 can play a important role in obtaining desirable decolorization kinetics.

Charcoal in either a honeycomb (HC) or disc (D) form is obtained from Mead Westvaco that could easily fit into the well of the Novelens case. A completely decolorized solution, is determined to have an absorbance of less than 0.03 AUs at 630 nm. When the lens care solution C2828-078 is exposed to either the disk or honeycomb over a 4 hour exposure time, the disk does a better job at decolorizing than the honeycomb

TABLE 3

|  | C-0 | C-1 | C-2 | C-3 | C-3-1 | C-5 | C-5-1 | C2828-068-A | C2828-068-B | C2828-078 |
|---|---|---|---|---|---|---|---|---|---|---|
| PHMB | 1.05 ppm | 1 ppm | 1 ppm | 1 ppm | 1 ppm | 1 ppm | 1 ppm | 1 ppm | 1 ppm | 1 ppm |
| 50% Dexpanthenol | 21 g/l | 0.41 g/L | 0.41 g/L | 0.41 g/L | 41 g/L | 0.41 g/l | 41 g/L | 40.0 g/L | 0.40 g/L | 0.41 g/L |
| Pluronic F 127 | 1.0 g/l |  |  |  |  |  |  | 1.0 g/L | 1.0 g/L | 1.0 g/L |
| EDTA | 0.250 g/l | 0.04 g/l | 0.04 g/l | 0.04 g/l | 0.04 g/L | 0.04 g/l | 0.04 g/L | 0.25 g/L | 0.04 g/L | 0.04 g/L |
| Sorbitol | 18.8 g/l | 25.00 g/l |  |  |  | 46.8 g/l | 46.8 g/l | 18.8 g/L | 40 g/L | 40.00 g/L |
| $NaH_2PO_4$ | 4.6 g/l |  | 3.0 g/l | 3.00 g/l | 3.00 g/l | 3.00 g/l | 3.00 g/l | 4.6 g/L | 4.6 g/L | 3.00 g/L |
| Tromethamine | 3.32 g/l |  | 1.66 g/l | 1.66 g/l | 1.66 g/l | 1.66 g/l | 1.66 g/l | 3.32 g/L | 3.32 g/L | 1.66 g/L |
| Xylitol USP/EP/JP |  | 20.00 g/l | 34.00 g/l | 34.00 g/l | 34.00 g/l |  |  |  |  |  |
| Pluronic F-87 |  | 1.00 g/l | 1.00 g/l | 1.00 g/l | 1.00 g/l | 1.00 g/l | 1.00 g/l |  |  |  |
| Tyloxapol |  | 0.20 g/l | 0.20 g/l |  |  |  |  |  |  | 0.20 g/L |
| Povidine |  | 2.00 g/l | 2.00 g/l |  |  |  |  |  |  | 2.00 g/L |
| Bis-Tris Propane |  | 1.37 g/l |  |  |  |  |  |  |  |  |
| FD & C Blue #1 | 1 mg/l | 1 mg/l | 1 mg/l | 1 mg/l | 1 mg/l | 1 mg/l | 1 mg/l | 1 mg/L | 1 mg/L | 1 mg/L |

EXAMPLE 6

Lens care solutions are prepared to have compositions shown in Table 4.
Carbon Decolorization Recycling Experiments are performed to determine how many cycles of decolorization can be achievable with a single source of carbon before the charcoal would no longer decolorize the colored lens care solution within the appropriate time window (4 hours). Novelens cases are used in the experiments with various forms of charcoal (BX 7540, RGC 20×50, TAC600, WVB 20×50, Norit RO×0.8) contained within a tea bag using 6.0 mL of a lens care solution. A total of 0.36 g of charcoal is used in the studies. With all of carbon studies, using formulation C2828-078, a total of 1-2 total cycles is achieved before the loss of decolorization is experienced.

over an extended period of time; however, does not consistently decolorize the sample. Where a 6 hour exposure time is used, complete decolorization is achieved for 10 consecutive cycles.

Number of decolorization cycles can be increased by changing the sorbitol to NaCl in the formulation, 10 decolorization cycles is achieved.
Antimicrobial Efficacy in the Presence of Charcoal Microbial efficacy of C2828-078 is determined in the presence or absence of charcoal BX7540, CAL 12×40, and WVB 1500 12×50. The results are shown in Tables 5a and 5b.

After a 6 hour exposure of the formulation 2860-075, which contains 2 ppm PHMB, to Acticarbon BX no 217, 0.51 ppm PHMB is still present in the solution.

The formulation 2828-078 (PDRS 28139) was tested for stand alone micro-efficacy a variety of charcoals (BX7540, TAC600, WVB 20×50, RGC 20×50)

TABLE 4

|  | Composition | | | |
|---|---|---|---|---|
| Components | C2828-078 | C2860-075 | C2860-099 | C2913-026 |
| PHMB | 1 ppm | 2 ppm | 1 ppm | 1 ppm |
| 50% Dexpanthenol | 0.41 g/L | 0.41 g/L | 0.41 g/L | 0.41 g/L |
| Pluronic F 127 | 1.0 g/L | 1.0 g/L |  | 1.00 g/L |
| EDTA | 0.04 g/L | 0.04 g/L | 0.04 g/L | 0.04 g/L |
| Sorbitol | 40.00 g/L | 40.00 g/L | 40.00 g/L |  |
| $NaH_2PO_4$ | 3.00 g/L | 3.00 g/L | 3.00 g/L | 3.00 g/L |
| Tromethamine | 1.66 g/L | 1.66 g/L | 1.66 g/L | 1.66 g/L |
| Tyloxapol | 0.20 g/L | 0.20 g/L | 0.20 g/L | 0.20 g/L |
| Povidine | 2.00 g/L | 2.00 g/L | 2.00 g/L | 2.00 g/l |
| FD & C Blue #1 | 1 mg/L | 1 mg/L | 1 mg/L | 1 mg/L |
| Pluronic 17R4 |  |  | 1.00 g/L |  |
| NaCl |  |  |  | 8.6 g/L |

TABLE 5a

| Organism | Charcoal | Reduction in Log | |
|---|---|---|---|
| | | 5 min | 4 hours |
| S. marcescens | Yes | 1.22 | 1.46 |
| S. marcescens | No | 2.08 | 1.93 |
| P. aeruginosa | Yes | 2.91 | 3.41 |
| P. aeruginosa | No | 3.05 | 5.87 |
| S. aureus | Yes | 1.84 | 2.44 |
| S. aureus | No | 2.43 | 5.62 |
| S. aureus | Yes | 1.28 | 1.72 |

TABLE 5b

| Organism | Charcoal | Reduction in Log | | |
|---|---|---|---|---|
| | | 5 min | 4 h | 24 h |
| C. albicans | Yes | 0.52 | 0.83 | 0.72 |
| C. albicans | No | 1.26 | 3.15 | 5.41 |
| F. solani | Yes | 0.21 | 1.45 | 1.50 |
| F. solani | No | 0.31 | 2.93 | 3.75 |

Charcoal tablets and/or honeycombs which had been previously purged with 100 ppm PHMB solution are tested for any anti-microbial activity. Charcoal disk and honeycomb configurations are soaked in 100 ppm PHMB. An additional set of charcoal disks and honeycomb material soaked in Phosphate Buffered Saline (PBS) is prepared to serve as controls. Each disc is aseptically removed from the PHMB or saline solution and placed in 10 ml sterile (PBS) for a period of 24 hours to purge any remaining PHMB disinfectant from the charcoal matrix. After the saline purge, each charcoal piece is aseptically removed from the PBS soaking solution and placed in a tube containing 10 ml sterile PBS. These tubes are then inoculated with bacteria or fungi to evaluate if any antimicrobial activity is imparted to the charcoal that has been saturated in PHMB. An additional saline control is also evaluated to rule out any inherent antimicrobial qualities of the charcoal itself.

The panel of bacterial and fungal organisms used in the study are specified in the ISO guidelines for disinfection of contact lenses. Following inoculation, the carbon and control tubes are incubated for a period of 24 hours. After the incubation period each carbon honeycomb or disk is removed from the organism suspension and transferred to an appropriate growth medium. The residual saline from each tube is then sampled to quantify any remaining organisms. Following an appropriate incubation period the carbon samples are observed for the presence or absence of microbial growth and the organisms recovered from the saline are quantitated. All carbon samples, test or control, are found to be positive for growth of the challenge organism. Enumeration of the saline soak saline solutions revealed no reduction for *Staphylococcus aureus*. *Serratia marcescens* increases in number during the 24 hour incubation period. A slight reduction in colony forming units of *Pseudomonas aeruginosa* is shown with 2 of 3 disk or honeycomb samples. A reduction in colony forming units is observed with *Candida albicans* in both test and control samples. A slight reduction in numbers is observed with *Fusarium solani* for all test disks and 2 of 3 honeycomb samples, the others demonstrate no reduction.

Cleaning Efficacy in the Presence of Charcoal

The cleaning efficacy of the formulation C2828-078 is tested both in the presence or absence of charcoal. Cleaning efficacy of the formulation in the presence of charcoal is decreased significantly. It is believed that this loss in cleaning efficacy is due to the non-specific absorption of many of the ingredients within the MPS formulation.

It is therefore preferably that a semi-permeable membrane should be used to minimize or eliminate non-specific absorption of ingredients other than colorants in a MPS formulation.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Furthermore, titles, headings, or the like are provided to enhance the reader's comprehension of this document, and should not be read as limiting the scope of the present invention. Accordingly, the spirit and scope of the appended claims should not be limited to the description of the preferred versions contained therein.

What is claimed is:

1. A lens care kit for cleaning and disinfecting contact lenses, comprising:
    a colored lens care solution including a water-soluble colorant and a microbiocidal compound; and
    a solid absorbing agent,
    wherein, when in contact with the colored lens care solution, the solid absorbing agent adsorbs the colorant over a time period sufficient to substantially discolor the colored lens care solution, thereby indicating that lenses under disinfecting and cleaning by the colored lens care solution are ready for use wherein the kit comprises a lens case having a well for holding a contact lens to be treated and an amount of the colored lens care solution, a compartment in fluid communication with the well, and a semi-permeable membrane is located between the well and the compartment, wherein the solid absorbing agent is activated charcoals and placed in the compartment of the lens case, wherein the semi-permeable membrane is capable of selectively or preferentially allowing the colorant to pass through so as to be absorbed by the charcoal in the compartment.

2. The lens care kit of claim 1, wherein the colored lens care solution is obtained immediately prior to treating the lens in the lens case by mixing two solutions, one hydrogen peroxide containing solution free of colorant and the other solution containing colorant and free of hydrogen peroxide.

3. The lens care kit of claim 1, wherein the colored lens care solution is a multiple purpose solution which is free of hydrogen peroxide.

4. The lens care kit of claim 3, wherein the microbiocidal compound is a hexamethylene biguanide polymer (PHMB) has a molecular weight at least 5 folder larger than that of the colorant, wherein the PHMB is present in an amount of from about 0.01 ppm to about 10 ppm.

5. The lens care kit of claim 4, wherein the colored lens care solution initially has a color of blue or green or purple.

6. The lens care kit of claim 5, wherein after the colored lens care solution is in contact with the solid absorbing agent, the color of the colored solution is gradually faded over a controlled time period.

7. The lens care kit of claim 6, wherein, at the end of the controlled time period, the color of the colored lens care solution is substantially disappeared and becomes substantially clear.

8. The lens care kit of claim 7, wherein the controlled time period is sufficiently long for disinfecting contact lenses.

9. The lens care kit of claim 8, wherein the controlled time period is at least about 2 hour.

10. The lens care kit of claim 8, wherein the controlled time period is at least about 4 hours.

11. The lens care kit of claim 8, wherein the controlled time period is at least about 6 hours.

12. The lens care kit of claim 1, wherein the colorant is modified to have a polymer covalently attached to the colorant so as to minimize the adsorption of the colorant by the contact lenses under treatment.

13. The lens care kit of claim 12, wherein the solid absorbing agent is placed into a pinwheel configuration within the confines of the lens case, wherein the pinwheel configuration is covered with a top with an opening that allows only a small piece of the pinwheel to be exposed to the lens care solution.

14. The lens care kit of claim 1, wherein the solid absorbing agent is placed into a pinwheel configuration within the confines of the lens case, wherein the pinwheel configuration is covered with a top with an opening that allows only a small piece of the pinwheel to be exposed to the lens care solution.

15. The lens care kit of claim 14, wherein the opening has a sector shape.

16. The lens care kit of claim 15, wherein the top of the pinwheel is capable of being rotated to allow a fresh amount of absorbing agent to be exposed to the lens care solution.

* * * * *